US00PP28186P3

(12) United States Plant Patent
Uchneat

(10) Patent No.: US PP28,186 P3
(45) Date of Patent: Jul. 11, 2017

(54) ***DAHLIA* PLANT NAMED 'G13518'**

(50) Latin Name: *Dahlia variabilis*
Varietal Denomination: G13518

(71) Applicant: Michael S. Uchneat, Bellefonte, PA (US)

(72) Inventor: Michael S. Uchneat, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 12 days.

(21) Appl. No.: 14/756,442

(22) Filed: Sep. 4, 2015

(65) Prior Publication Data

US 2017/0071105 P1 Mar. 9, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

National Gardening Association Plants Database *Dahlia* (*Dahlia* Dahlightful Georgia Peach 2016, retrieved on Nov. 2, 2016, retrieved from the Internet at <http://garden.org/plants/view/710312/Dahlia-Dahlia-Dahlightful-Georgia-Peach/> pp. 1-3.*
Proven Winners Dahlightful Georgia Peach Tag Image 2016 retrieved on Nov. 2, 2016, retrieved from the Internet at <https://www.provenwinners.com/images/dahlightful-georgia-peach-tagimagejpg> pp. 1-3.*

* cited by examiner

*Primary Examiner* — June Hwu
(74) *Attorney, Agent, or Firm* — C. A. Whealy

(57) ABSTRACT

A new and distinct cultivar of *Dahlia* plant named 'G13518', characterized by its compact, upright and mounding plant habit; vigorous growth habit; freely branching habit; dense and bushy appearance; very dark green-colored leaves; early and freely flowering habit; and semi-double type inflorescences with apricot and yellow-colored ray florets.

1 Drawing Sheet

Botanical designation: *Dahlia variabilis.*
Cultivar denomination: 'G13518'.

BACKGROUND OF THE INVENTION

The present invention relates to a new and distinct cultivar of *Dahlia* plant, botanically known as *Dahlia variabilis* and hereinafter referred to by the name 'G13518'.

The new *Dahlia* plant is a product of a planned breeding program conducted by the Inventor in Bellefonte, Pa. The objective of the breeding program is to create new vigorous *Dahlia* plants that have dark-colored leaves, large attractive inflorescences and reduced sensitivity to Powdery Mildew.

The new *Dahlia* plant originated from a cross-pollination in Bellefonte, Pa. in October, 2012 of a proprietary selection of *Dahlia variabilis* identified as code number 3169-1-5M-2, not patented, as the female, or seed, parent with a proprietary selection of *Dahlia variabilis* identified as code number 3169-1-5M-1, not patented, as the male, or pollen, parent. The new *Dahlia* plant was discovered and selected by the Inventor as a single flowering plant from within the progeny of the stated cross-pollination in a controlled greenhouse environment in Bellefonte, Pa. in July, 2013.

Asexual reproduction of the new *Dahlia* plant by vegetative terminal cuttings in a controlled greenhouse environment in Bellefonte, Pa. since August, 2013 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G13518'. These characteristics in combination distinguish 'G13518' as a new and distinct *Dahlia* plant:

1. Compact, upright and mounding plant habit.
2. Vigorous growth habit.
3. Freely branching habit; dense and bushy appearance.
4. Very dark green-colored leaves.
5. Early and freely flowering habit.
6. Semi-double type inflorescences with apricot and yellow-colored ray florets.

Compared to plants of the female parent selection, plants of the new *Dahlia* differ primarily in the following characteristics:

1. Plants of the new *Dahlia* have semi-double type inflorescences whereas plants of the female parent selection have single type inflorescences.
2. Plants of the new *Dahlia* and the female parent selection differ in ray floret color as ray florets of plants of the female parent selection are uniformly yellow in color.

Compared to plants of the male parent selection, plants of the new *Dahlia* differ primarily in the following characteristics:

1. Leaves of plants of the new *Dahlia* are darker in color than leaves of plants of the male parent selection.
2. Plants of the new *Dahlia* and the male parent selection differ in ray floret color as plants of the male parent selection have bright rose pink-colored ray florets.

Plants of the new *Dahlia* can be compared to plants of *Dahlia* 'Mystic Fantasy', disclosed in U.S. Plant Pat. No. 25,417. In side-by-side comparisons conducted in Bellefonte, Pa., plants of the new *Dahlia* differed primarily from plants of 'Mystic Fantasy' in the following characteristics:

1. Plants of the new *Dahlia* were more freely branching than plants of 'Mystic Fantasy'.
2. Leaves of plants of the new *Dahlia* were lighter in color than leaves of plants of 'Mystic Fantasy'.
3. Plants of the new *Dahlia* had semi-double type inflorescences whereas plants of 'Mystic Fantasy' had single type inflorescences.

Plants of the new *Dahlia* can be compared to plants of *Dahlia* 'HDLE105', disclosed in U.S. Plant Pat. No. 25,053. In side-by-side comparisons conducted in Bellefonte, Pa., plants of the new *Dahlia* differed primarily from plants of 'HDLE105' in the following characteristics:

1. Leaves of plants of the new *Dahlia* were lighter in color than leaves of plants of 'HDLE105'.
2. Plants of the new *Dahlia* had semi-double type inflorescences whereas plants of 'HDLE105' had single type inflorescences.
3. Plants of the new *Dahlia* and 'HDLE105' differed in ray floret color as plants of 'HDLE105' had light yellow-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the right side of the sheet is a side perspective view of a typical flowering plant of 'G13518' grown in a container.

The photograph on the left side of the sheet is a close-up view of a typical flowering plant of 'G13518'.

DETAILED BOTANICAL DESCRIPTION

The aforementioned photographs and the following observations and measurements describe plants grown during the spring and summer in 10-cm containers in an outdoor nursery in Bonsall, Calif. and under cultural practices typical of commercial potted *Dahlia* production. During the production of the plants, day temperatures averaged 24° C., night temperatures averaged 10° C. and light levels ranged from 7,000 to 10,000 foot-candles. Plants were pinched two times and were 13 weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'G13518'.

Parentage:

*Female, or seed, parent.*—Proprietary selection of *Dahlia variabilis* identified as code number 3169-1-5M-2, not patented.

*Male, or pollen, parent.*—Proprietary selection of *Dahlia variabilis* identified as code number 3169-1-5M-1, not patented.

Propagation:

*Type.*—By vegetative terminal cuttings.

*Time to initiate roots, summer.*—About 7 to 10 days at ambient temperatures about 22° C. to 27° C.

*Time to initiate roots, winter.*—About 10 to 14 days at ambient temperatures about 18° C. to 23° C.

*Time to produce a rooted plant, summer.*—About three to four weeks at ambient temperatures about 22° C. to 27° C.

*Time to produce a rooted plant, winter.*—About four weeks at temperatures about 18° C. to 23° C.

*Root description.*—Medium in thickness, fleshy and fibrous; close to white to creamy white in color, actual color of the roots is dependent on substrate composition, water quality, fertilizers, substrate temperature and age of roots; tuber development has not been observed on plants of the new *Dahlia*.

*Rooting habit.*—Freely branching; medium density.

Plant description:

*Plant and growth habit.*—Compact, upright and mounding plant form; rounded inverted triangle; freely branching habit with about 14 lateral branches developing per plant, each lateral with potentially two secondary laterals developing per node; pinching enhances lateral branch development; inflorescences held above the foliar plane on strong peduncles; bushy and dense appearance; vigorous growth habit.

*Plant height.*—About 24.5 cm.

*Plant diameter or spread.*—About 25 cm.

*Lateral branches.*—Length: About 22.5 cm. Diameter: About 5 mm to 8 mm. Internode length: About 2.4 cm. Strength: Strong. Aspect: Erect to somewhat outwardly spreading. Texture: Scattered and sparse pubescence; woody with development. Luster: Matte. Color, developing: Close to 187A. Color, developed: Close to 199C.

Leaf description:

*Arrangement.*—Opposite; simple.

*Length.*—About 5.5 cm.

*Width.*—About 4 cm.

*Shape.*—Elliptical to oval.

*Apex.*—Acute.

*Base.*—Attenuate.

*Margin.*—Crenate to serrate.

*Venation pattern.*—Pinnate.

*Texture, upper surface.*—Smooth, glabrous.

*Texture, lower surface.*—Scattered and sparse pubescence; prominent venation.

*Luster, upper and lower surfaces.*—Matte.

*Color.*—Developing leaves, upper surface: Close to 203B. Developing leaves, lower surface: Slightly more green than N189B. Fully expanded leaves, upper surface: Darker than 147A; venation, close to 183B. Fully expanded leaves, lower surface: Close to 147B; venation, close to N137B.

*Petioles.*—Length: About 2.8 cm. Diameter: About 4 mm. Strength: Strong. Texture, upper and lower surfaces: Smooth, glabrous. Luster, upper and lower surfaces: Glossy. Color, upper surface: Close to 200A. Color, lower surface: Close to 200B.

Inflorescence description:

*Appearance and arrangement*.—Semi-double inflorescence form with ray florets forming acropetally on a receptacle; inflorescences positioned above the foliar plane on strong peduncles; inflorescences face mostly upright to outwardly; freely flowering habit with about 34 inflorescence buds and open inflorescences at one time.

*Fragrance*.—None detected.

*Time to flower*.—Early flowering habit, plants begin flowering about five weeks after planting; plants flower continuously from late spring through the autumn in Southern California.

*Post-production longevity*.—Inflorescences maintain good substance for about five days on the plant; inflorescences persistent.

*Inflorescence buds*.—Height: About 2.2 cm. Diameter: About 1.4 cm. Shape: Ovoid. Color: Close to N199C.

*Inflorescence size*.—Diameter: About 5.6 cm. Depth (height): About 2.8 cm. Disc diameter: About 2.2 cm.

*Receptacles*.—Height: About 1.1 cm. Diameter: About 3 cm. Shape: Flattened bowl-shape. Color: Close to N199B.

*Ray florets*.—Quantity per inflorescence: About nine to ten arranged in one to two whorls. Length: About 2.8 cm. Width: About 1.5 cm. Shape: Oval to nearly round. Apex: Emarginate. Base: Attenuate. Margin: Entire. Aspect: Initially upright to roughly perpendicular to the peduncle; somewhat concave. Texture, upper surface: Shallowly ridged, glabrous. Texture, lower surface: Smooth, glabrous. Luster, upper and lower surfaces: Matte. Color: When opening, upper surface: Close to N167C to N167D. When opening, lower surface: Close to 165C. Fully opened, upper surface: Close to 163B tinted with close to 167C. Fully opened, lower surface: Close to 162A to 162B.

*Disc florets*.—Quantity per inflorescence: About 84. Length: About 1.4 cm. Diameter: About 3 mm. Shape: Tubular, elongated; apices acute. Texture: Smooth, glabrous. Luster: Somewhat glossy. Color, when opening: Apex: Close to N167A. Mid-section: Close to N167C. Base: Close to 147C. Color, fully opened: Apex: Close to N170A. Mid-section: Close to N167C. Base: Close to 147C.

*Phyllaries*.—Quantity per inflorescence: About 15 arranged in two whorls; inner whorl with ten phyllaries and outer whorl with five smaller phyllaries. Inner whorl: Length: About 1.5 cm. Width: About 6 mm. Shape: Oblong to broadly lanceolate. Apex: Acute. Base: Truncate. Margin: Entire. Texture, upper and lower surfaces: Smooth, glabrous. Luster, upper and lower surfaces: Satiny, matte. Color, upper surface: Close to N199B. Color, lower surface: Close to N199C. Outer whorl: Length: About 8 mm. Width: About 4 mm. Shape: Elliptical. Apex: Acute. Base: Truncate. Margin: Entire. Texture, upper and lower surfaces: Smooth, glabrous. Luster, upper and lower surfaces: Satiny, matte. Color, upper surface: Darker than 147A. Color, lower surface: Close to 203B.

*Peduncles*.—Length, terminal peduncle: About 8.4 cm. Diameter: About 2 mm. Aspect: Mostly erect. Strength: Strong. Texture: Smooth, glabrous. Luster: Matte. Color: Close to 200A.

*Reproductive organs*.—Present on disc florets only; ray florets without visible reproductive organs. Androecium: Quantity per floret: Five. Filament length: About 2 mm. Filament color: Close to 145D. Anther shape: Lanceolate. Anther length: About 2.5 mm. Anther color: Close to 163B. Pollen amount: Moderate. Pollen color: Close to 17A. Gynoecium: Quantity per floret: One. Pistil length: About 9 mm. Style length: About 4 mm. Style color: Close to 15B. Stigma shape: Tri-parted. Stigma color: Close to 15B. Ovary color: Close to 145D.

*Seeds and fruits*.—Seed and fruit development have not been observed on plants of the new *Dahlia*.

Disease & pest resistance: Plants of the new *Dahlia* have not been observed to be resistant to pathogens and pests common to *Dahlia* plants.

It is claimed:

1. A new and distinct *Dahlia* plant named 'G13518' as illustrated and described.

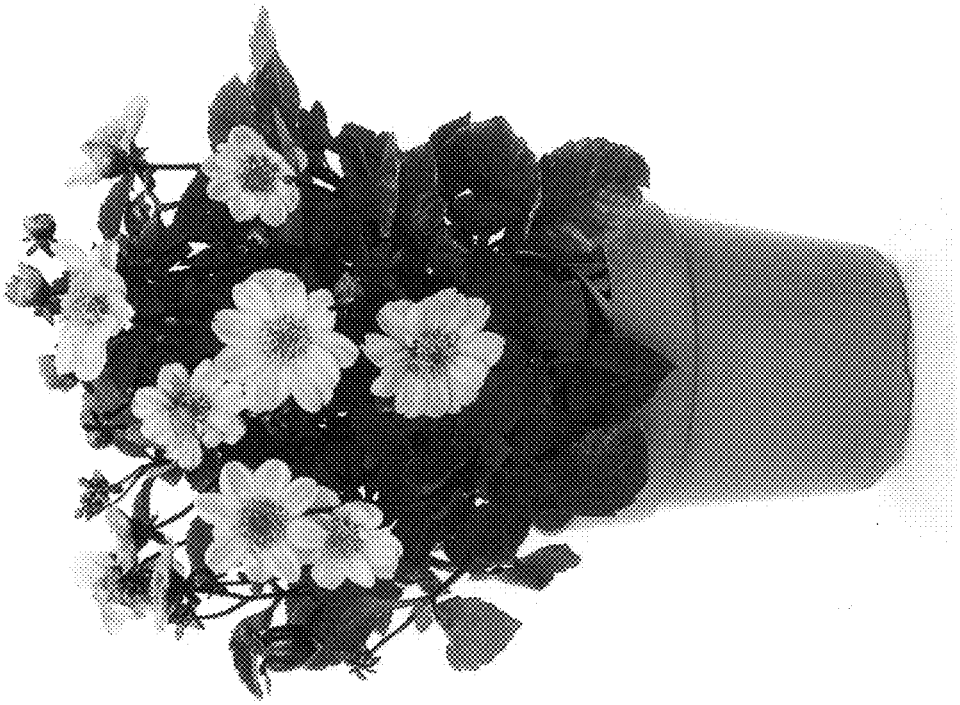
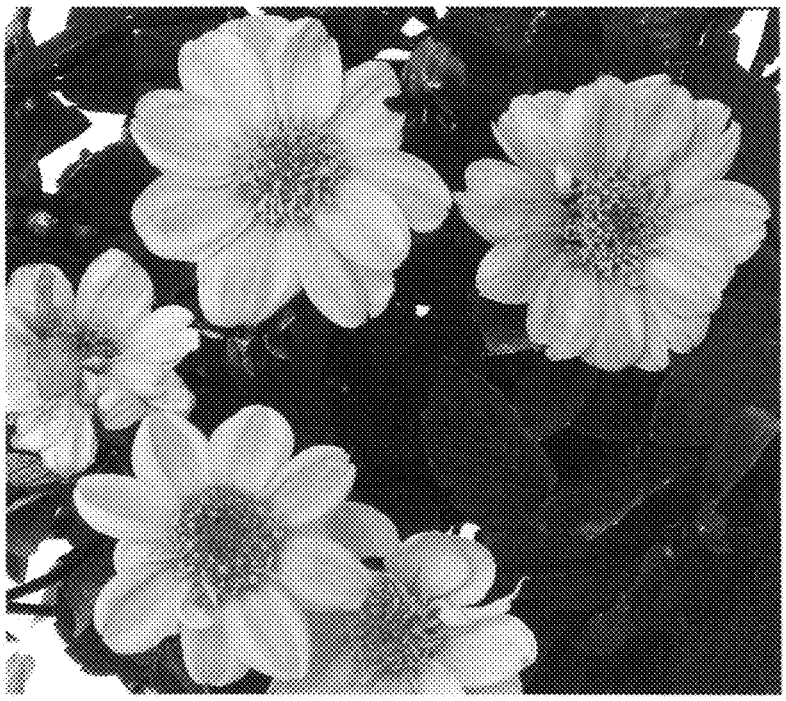

* * * * *